(12) United States Patent
Öz (10) Patent No.: US 7,381,170 B2
(45) Date of Patent: Jun. 3, 2008

(54) APPARATUS FOR EXERCISING THE ABDOMINAL MUSCLES IN A SITTING POSITION

(75) Inventor: Sadik Öz, Nürnberg (DE)

(73) Assignee: SOZ, Nurnberg (DE)

( * ) Notice: Subject to any disclaimer, the term of this patent is extended or adjusted under 35 U.S.C. 154(b) by 17 days.

(21) Appl. No.: 11/269,345

(22) Filed: Nov. 8, 2005

(65) Prior Publication Data

US 2006/0116251 A1  Jun. 1, 2006

(30) Foreign Application Priority Data

Nov. 14, 2004  (DE) .................... 10 2004 055 235

(51) Int. Cl.
*A63B 26/00*  (2006.01)

(52) U.S. Cl. ...................................... 482/140; 482/148

(58) Field of Classification Search ................ 482/140, 482/35–38; D2/627; 24/31 R; 182/3; 244/122 B; 297/464; 180/268; 280/801.1; D11/200
See application file for complete search history.

(56) References Cited

U.S. PATENT DOCUMENTS

| | | | |
|---|---|---|---|
| 5,743,838 A * | 4/1998 | Willis | 482/124 |
| 5,857,984 A * | 1/1999 | deBoer et al. | 600/595 |
| 6,520,893 B2 * | 2/2003 | Bray | 482/140 |
| 7,077,794 B1 * | 7/2006 | Bray | 482/140 |
| 2005/0194830 A1 * | 9/2005 | Kohani | 297/464 |

* cited by examiner

Primary Examiner—Lori Amerson
(74) Attorney, Agent, or Firm—Pandiscio & Pandiscio (57) ABSTRACT

An apparatus for exercising abdominal muscles in a sitting position, the apparatus including an elastic belt that constrains the abdomen by exerting tensile force and is moved by the user by active muscular exertion, and to a system for detachably fastening the belt to a backrest of a chair, car seat, or the like.

11 Claims, 7 Drawing Sheets

APPARATUS FOR EXERCISING THE ABDOMINAL MUSCLES IN A SITTING POSITION

BACKGROUND OF THE INVENTION

1. Field of the Invention

The invention is directed to an apparatus for exercising the abdominal muscles in a sitting position, comprising an at least regionally elastic belt that constrains the abdomen by exerting tensile force and is moved by the user by active muscular exertion.

2. Description of the Prior Art

Known from DE OS [Offenlegungsschrift; Unexamined Laid-Open Patent Application] 100 06 588 A1 is a girdle-type belt for improving the posture and for exercising the abdominal muscles, which is worn around the waist and comprises a tensile force sensor which on excessive relaxation of the abdominal muscles triggers an alarm to remind the wearer of the belt to contract the abdominal muscles.

This girdle-type belt is preferably worn under an article of clothing by the person concerned and is therefore intended to remain continually on the body. It is optimized for this specific application and cannot be used to exercise other muscles, especially since only a comparatively short segment of the belt is actually elastic and greater expansion is therefore not possible.

Furthermore, in the unused state there is no defined way of keeping the belt at a specific location where it could quickly be retrieved.

SUMMARY OF THE INVENTION

From the disadvantages of the described prior art comes, therefore, the problem initiating the invention, that of improving an apparatus of the above species for exercising the abdominal muscles in a sitting position so that the tensile belt can be taken off quickly at any time and is still always ready for use or, optionally, can even be used to exercise other muscles.

To solve this problem, the invention provides a system for preferably detachably affixing the tensile belt to the backrest of a chair, car seat, or other article of seating furniture.

It is precisely when sitting comfortably in a car or at the office that one is all-too-readily inclined to relax the abdominal muscles completely so that they gradually go slack. Consequently, a tensile belt for exercising the abdominal muscles is especially important when sitting, whereas when walking or standing the abdominal muscles are tensed constantly anyway in order to maintain the balance. The fact that the belt can be fastened to a chair or seat therefore means that it can always be put on, and is therefore available for exercising the abdominal muscles, on sitting down. This is advantageous particularly in the case of automobile travel, where there are no other movement options during relatively long trips and exercising the abdominal muscles keeps the circulation flowing as well.

It has proven favorable for the length of the elastic belt to be adjustable. For example, when used in a vehicle, the belt can in this way be adapted to the various builds of different drivers or passengers. The length adjustment can be effected for example by guiding a variable portion of the belt, in a double layer, past an adjustable buckle or the like.

The tensile belt itself need encircle the waist of a person only partially, preferably over no more than 270° or less; the remainder of the waist is embraced by the fastening system, which is affixed to the backrest of the chair or seat concerned.

According to a preferred improvement of the invention, the tensile belt comprises a device for detecting tensile force. This makes it possible to count and/or otherwise assign a value to the contractions of the abdominal muscles performed by the wearer. If desired, the device for detecting tensile force can also be detachably connected or retrofittable/connectable.

A connecting means, for example a mating connector element, can be disposed at one or preferably each end of the tensile belt. The tensile belt can thus be detached partially or completely from the fastening arrangement. If only one end is detached, then the tensile belt remains ready for use on the seat concerned, but the person can still stand up and leave his or her seat. If both ends are detached, the tensile belt can be detached from the seat and used elsewhere, for example in the manner of an expander for exercising the arm muscles or the like.

As a counterpart to the connecting means at one or both ends of the tensile belt, the system for affixing the belt to the backrest of a seat also comprises at least one connecting means, for example a mating connector element, which is compatible with the mating connector element on the elastic belt.

The connecting means between the tensile belt on the one hand and the system for affixing the latter to the backrest of a seat on the other hand should be provided with detent elements to prevent unwanted disconnection of the connecting means. These can be elastically deflectable tongues disposed on a connecting means and each provided at its free end with one or more hook-shaped prolongations, which in the relaxedly sprung-back state extend behind a complementary projection or other prolongation on the opposite connecting means and can be disconnected only by manually pressing the resilient tongues elastically away and/or back.

An advantageous improvement of the invention is to provide a lordosis support on the system for affixing the tensile belt to the backrest of a chair, car seat or similar article of seating furniture. Such a support for the lumbar spine serves to straighten the posture and thus helps to save wear and tear on the spinal column, a measure that is to be regarded as an ideal precaution for good health in old age.

The invention recommends arranging the lordosis support between two connecting means for the tensile belt. In this way, the tensile belt always rests symmetrically in front of the lordosis support and creates optimum conditions for exercising in a manner that benefits all muscle parts equally.

The lordosis support can be implemented as a cushion. A cushion provided with a relatively fixed core is suitable for this purpose, but another suitable expedient is an inflatable air cushion that can be blown up by mouth through a valve like an inner-tube-type float or beach ball or in the manner of an air balloon, or can be filled by means of an air pump. An air cushion has the advantage that for people who do not want the lordosis function, it can be emptied with a quick maneuver and then collapsed so that it is flat and therefore imperceptible.

A particularly simple construction is obtained when the system for affixing the tensile belt to a seat embraces the backrest thereof. This produces a positive fit, which—in combination with the earth's gravity—reliably prevents unwanted detachment. Dimensioning the amplitude of the fastening system (in the relaxed state) to be slightly smaller than the amplitude of a cross section through the backrest results in a positive fit that is largely free of play.

If such a fastening belt is, in addition, elastically implemented (to a limited extent), then it tightens around the backrest and lies against it under a more or less great contact pressure and thus in a frictionally engaged manner, so that any independent slippage is inhibited as well.

To this end, the belt extending around the backrest of a chair, car seat or the like comprises on its inner face a slip-inhibiting surface or coating. In this way, even a moderate contact pressure is sufficient to affix the fastening belt to a seat.

In a first embodiment of the invention, the system for affixing the tensile belt to the backrest of a chair, car seat or the like is implemented as a belt, strap, hood or the like that is fastened to itself and can be slipped over the backrest concerned. In such cases it could even serve as a protective covering for the backrest. The handling is extremely simple.

In another embodiment, the system for affixing the tensile belt to the backrest of a chair, car seat or the like is implemented as a belt, strap or the like that is able to be fastened to itself and can be placed around the backrest concerned. This results in a minimal arrangement that can be installed with few manipulations but can also be removed just as quickly.

The belt extending around the backrest of a chair, car seat or the like can be composed of more than one part, for example in order to connect an elastic part to nonelastic or less elastic segments, for example in the region of a lordosis support.

Finally, the invention is distinguished by two grip elements, each comprising a connecting means, for example a mating connector element, for connection each to a respective compatible connecting means disposed at a respective end of the tensile belt. When provided with grips of this kind, the tensile belt becomes an expander and can be used for a wide variety of exercises for the arms and/or legs.

BRIEF DESCRIPTION OF THE DRAWINGS

Additional features, details, advantages and actions based on the invention will emerge from the following description of preferred embodiments of the invention and from an examination of the drawings, wherein.

DESCRIPTION OF THE PREFERRED EMBODIMENTS

The inventive apparatus 1 for exercising the abdominal muscles in a sitting position includes four parts: an elastic, tensile-force-absorbing belt 2, a belt 3 to affix the latter to the backrest of a seat, and two grip elements 4, 5.

Figure 4:
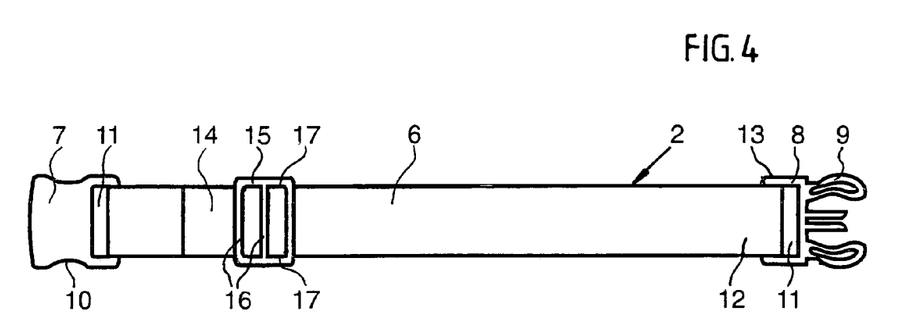
FIG. 4 is an elevational view showing a tensile belt portion of the apparatus in one of its broad sides.

The tensile belt 2 is comprised of an elastic strap 6 extending between two connecting means 7, 8. The two connecting means 7, 8 are implemented as mutually complementary mating connector elements, so tensile belt 2 could also be fastened to itself, although this is not contemplated for the purposes of its intended use.

Mating connector element 7, depicted on the left in FIG. 4, is constructed in the manner of a belt clasp with a slit-shaped opening on its side facing away from tensile belt 2, for the insertion of mating connector element 8. The latter includes two mutually confronting resilient tongues 9, which are able to deflect elastically inward when inserted in belt clasp 7 in order to fit through a there-provided inwardly projecting edge provided at the mouth of the slit-shaped opening.

Beyond, and thus inward of, this edge they then immediately deflect outward again and are then unable to disconnect on their own. However, provided on the narrow sides 10 of clasp 7 are openings at which a person can press the resilient tongues 9 inward in order to withdraw clasp tongue 8 from belt clasp 7.

Each of the two mating connector elements 7, 8 comprises on its back face a slit 11 for the passage of tensile belt 2. A throughpassing end 12 of tensile belt 2 is then looped around a crosspiece 13 partially delimiting the slit 11 concerned and is, for example, stitched to itself.

Before an opposite end 14 of tensile belt 2 is threaded through slit 11 on the other mating connector element 7, a buckle 15 is pushed onto tensile belt 2. Buckle 15 is comprised of three mutually parallel crosspieces 16 and two legs 17 joining their proximate ends to one another. Tensile belt 2 is threaded through both openings between two crosspieces 16 at a time. The still-free end 14 of the tensile belt is thereupon pushed through slit 11 of second mating connector element 7, then guided back to buckle 15, and is there, in addition to the middle portion of tensile belt 2, pushed through both openings in the buckle. Finally, it is looped around the middle crosspiece 16 and stitched to itself. By sliding buckle 15 along tensile belt 2, the length thereof can be varied and adapted to the girth of any person.

Figure 2:
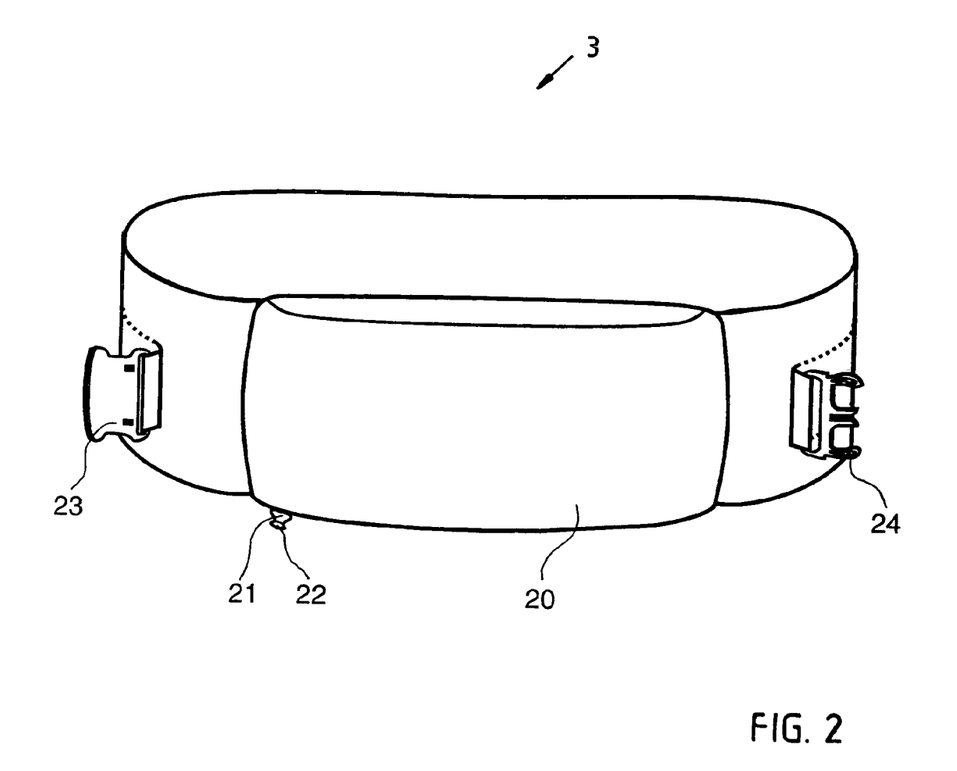
FIG. 2 is a front perspective view of the fastening system of the apparatus of FIG. 1.

Fastening belt 3 is provided with a lordosis support 20, which in the example shown is implemented as a cushion that can be filled with air. For filling purposes, a valve 21 with a removable stopper 22 is provided. In the inflated state, air cushion 20 extends across almost the entire width of backrest 18; the height extent of cushion 20 is roughly equal to or slightly greater than the width of fastening belt 3. Such a cushion can be attached to the front segment of fastening belt 3, but can also be an integral part thereof. To this extent, such a lordosis cushion 20 can optionally also assume the function of the elastic portion of fastening belt 3.

Fastening belt 3 is provided with a lordosis support 20, which in the example shown is implemented as a cushion that can be filled with air. For filling purposes, a valve 21 with a removable stopper 22 is provided. In the inflated state, air cushion 20 extends across almost the entire width of backrest 18; the height extent of cushion 20 is roughly equal to or slightly greater than the width of fastening belt 3. Such a cushion can be attached to the front segment of fastening belt 3, but can also be an integral part thereof. To this extent, such a lordosis cushion 20 can optionally also assume the function of the elastic portion of fastening belt 3.

On either side of lordosis support 20, fastening belt 3 is provided with a mating connector element 23, 24, each of which is compatible with a respective mating connector element 7, 8 of tensile belt 2. The elastic region of fastening belt 3 is preferably located at the front of the belt, between mating connector elements 23, 24, while the back portion of fastening belt 3, particularly beyond the two mating connector elements 23, 24, is implemented as nonelastic and therefore neither stretches nor shifts as the abdominal muscles are exercised. The two mating connector elements 23, 24 need not connect directly laterally to lordosis support 20. Rather, there can be provided interjacently in each case a preferably elastic portion that serve(s) to adapt the amplitude of the belt to the amplitude of the backrest concerned. The lordosis support in this case is comparatively narrow and chiefly supports the lumbar spine itself.

Figure 3:
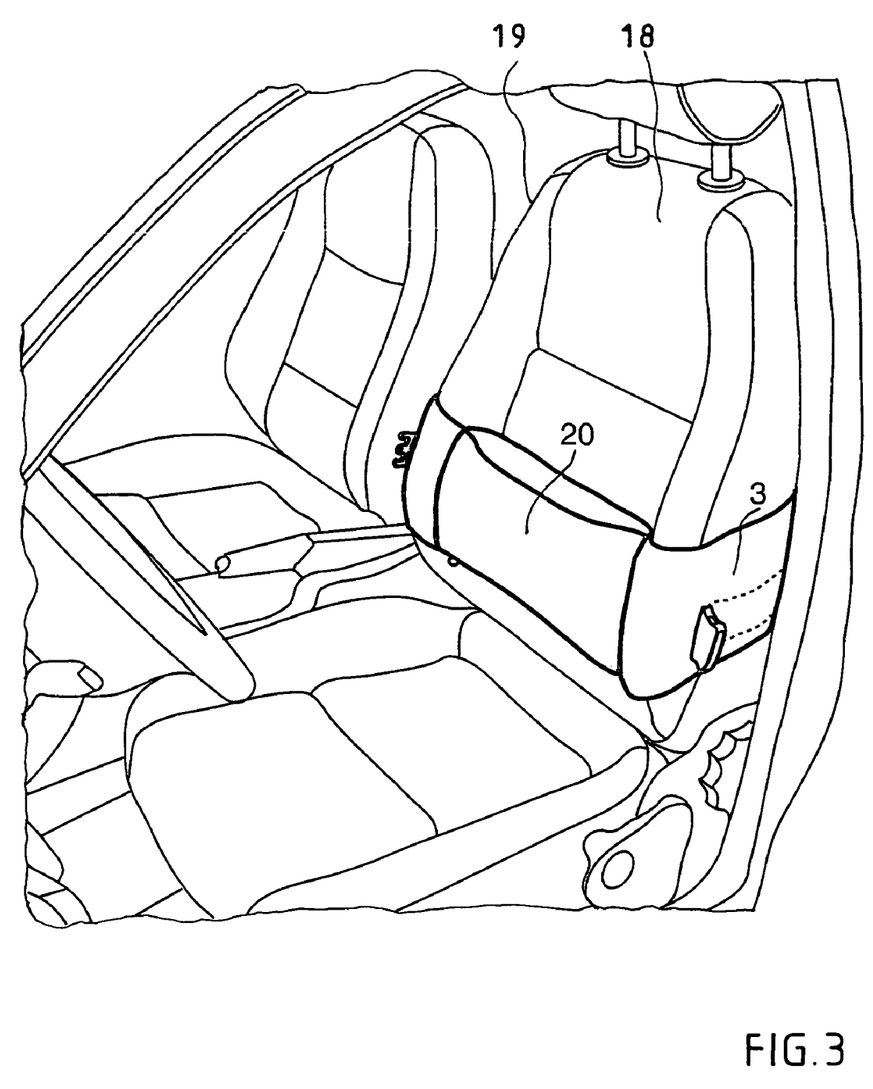
FIG. 3 is a perspective view showing the fastening system of FIG. 2 affixed to a car seat.

Once a person has sat down on the vehicle seat 19 depicted in FIG. 3, tensile belt 2 can be connected to fastening belt 3 and the exercising of the abdominal muscles can commence. If the person concerned wishes to leave the vehicle for a short time, for example to fill up the gas tank, only one mating connector element 7, 8 need be disconnected from fastening belt 3; tensile belt 2 then remains in the car and can be donned and used again as soon as the person gets back in.

Figure 5:
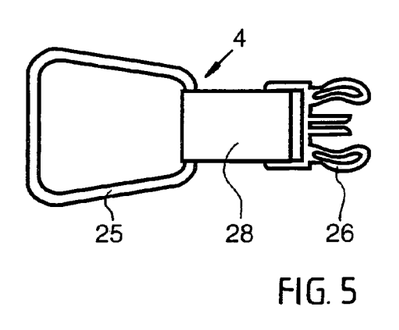
FIG. 5 is a side elevational view of a grip piece for connection to the tensile belt of FIG. 4.
Figure 6:
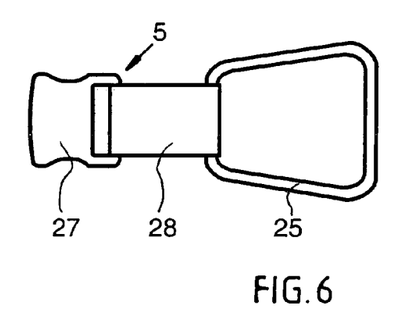
FIG. 6 is a side elevational view showing a second grip piece for connection to the tensile belt of FIG. 4.

If, on the other hand, both mating connector elements 7, 8 are disconnected from fastening belt 3, then the two grip elements 4, 5 can instead each be connected to a respective end 12, 14 of tensile belt 2. Each of the two grip elements 4, 5 is comprised of a ring-shaped grip 25 fastened to itself and made, for example, from a round bar bent and welded to assume a trapezoidal, rectangular or square outline, and further of a mating connector element 26, 27 designed to interlock with a respective mating connector element 7, 8 of tensile belt 2, and of a short loop 28 passing through grip 25 and connector element 26, 27. The mating connector elements 26, 27 of the two grip elements 4, 5 are also complementary to each other.

Figure 1:
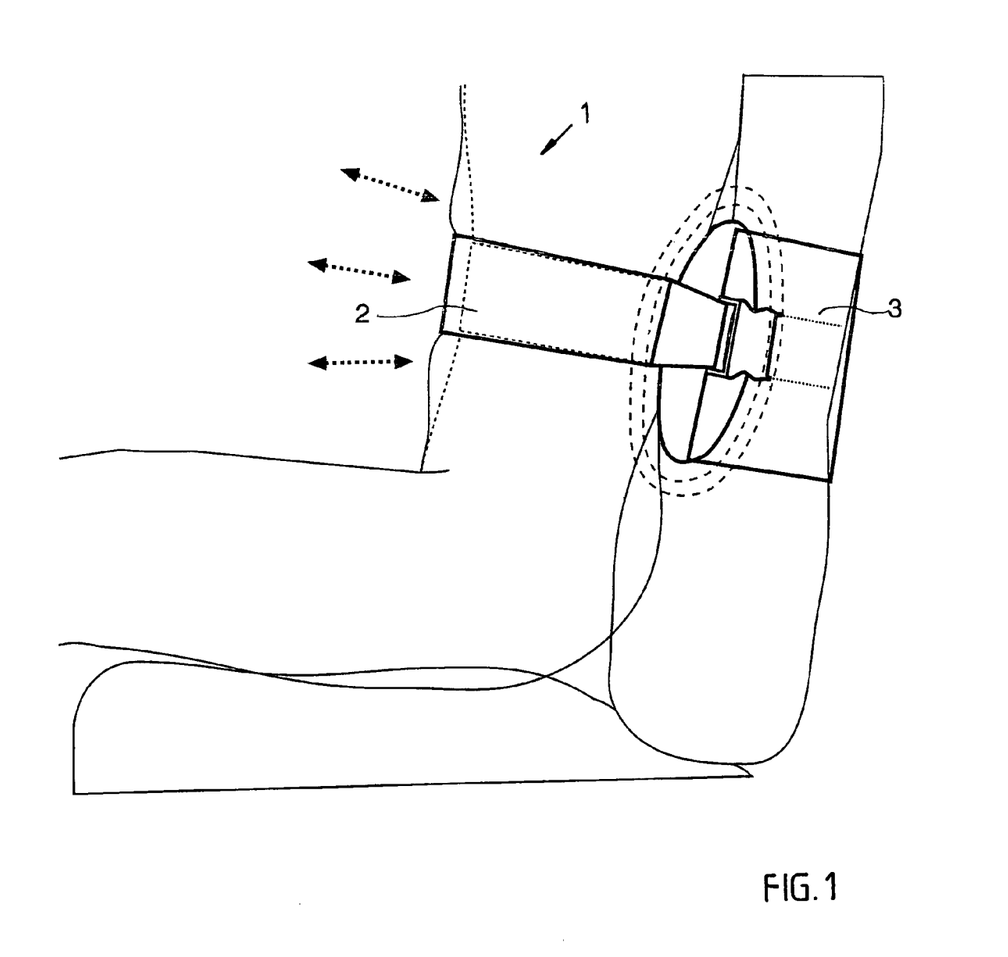
FIG. 1 is a side elevational view of an inventive apparatus fastened to the backrest of a car seat and being used by a person.
Figure 7:
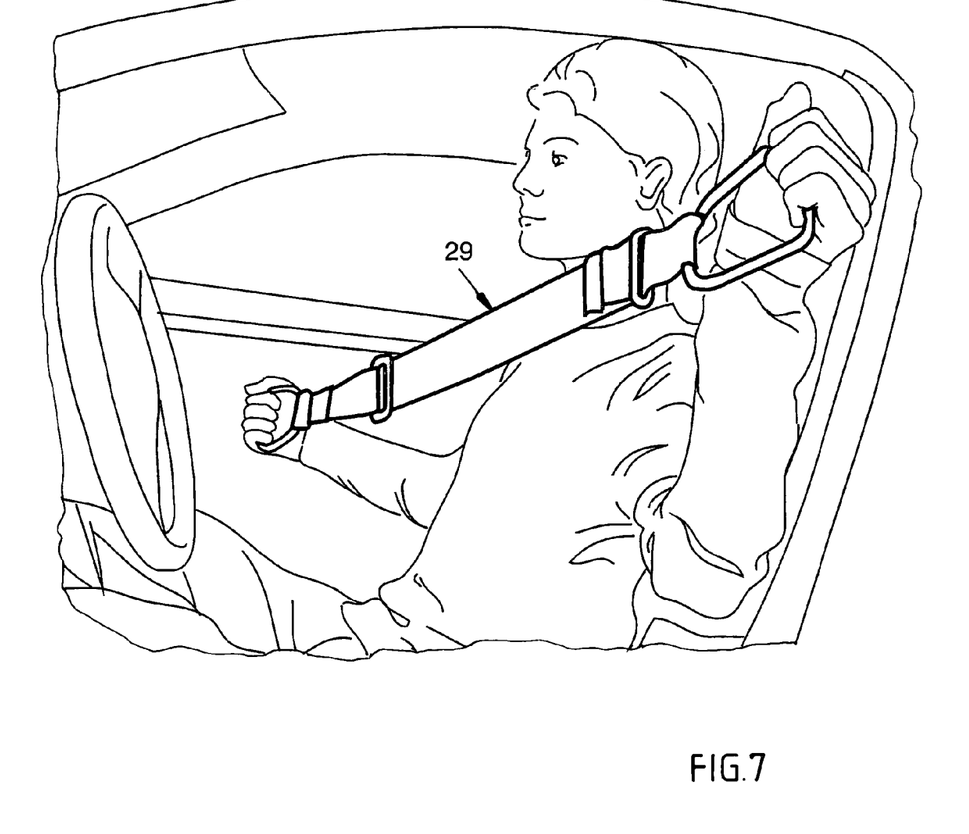
FIGS. 7-9 are perspective views showing a person performing various exercises with the tensile belt of FIG. 4, in combination with the grip pieces of FIGS. 5 and 6.
Figure 8:
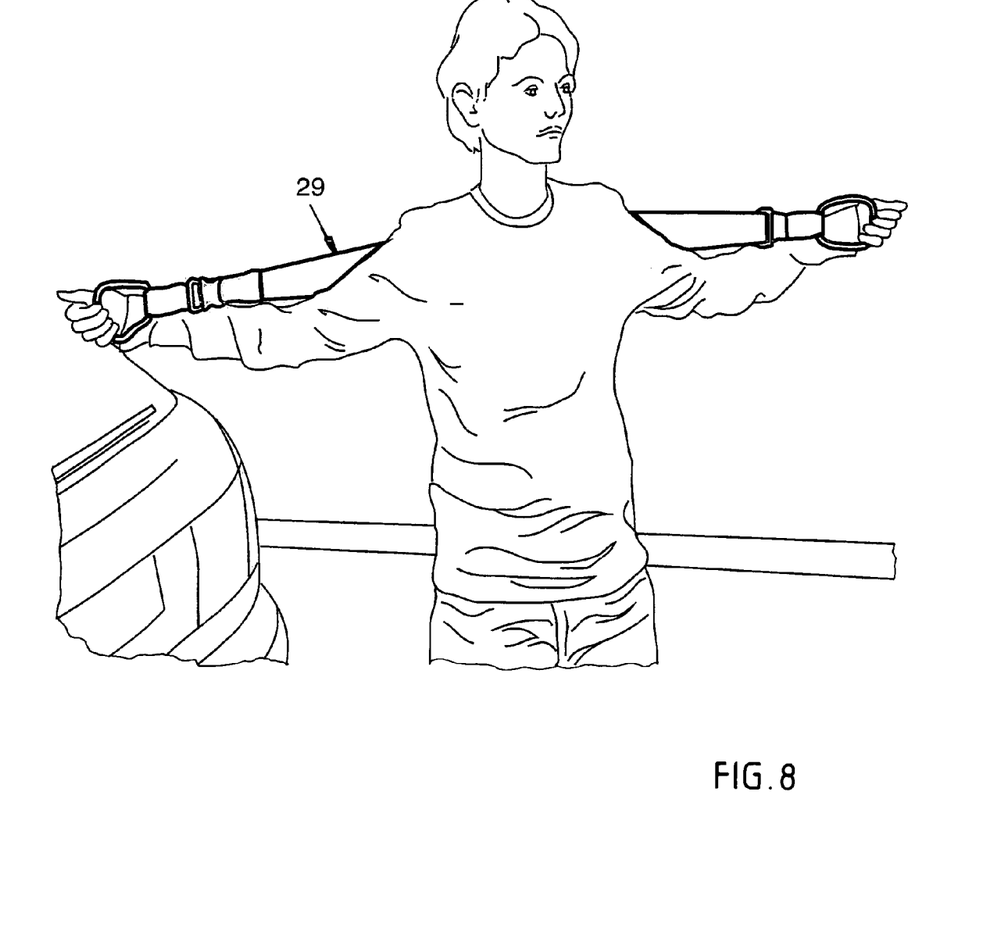
Figure 9:
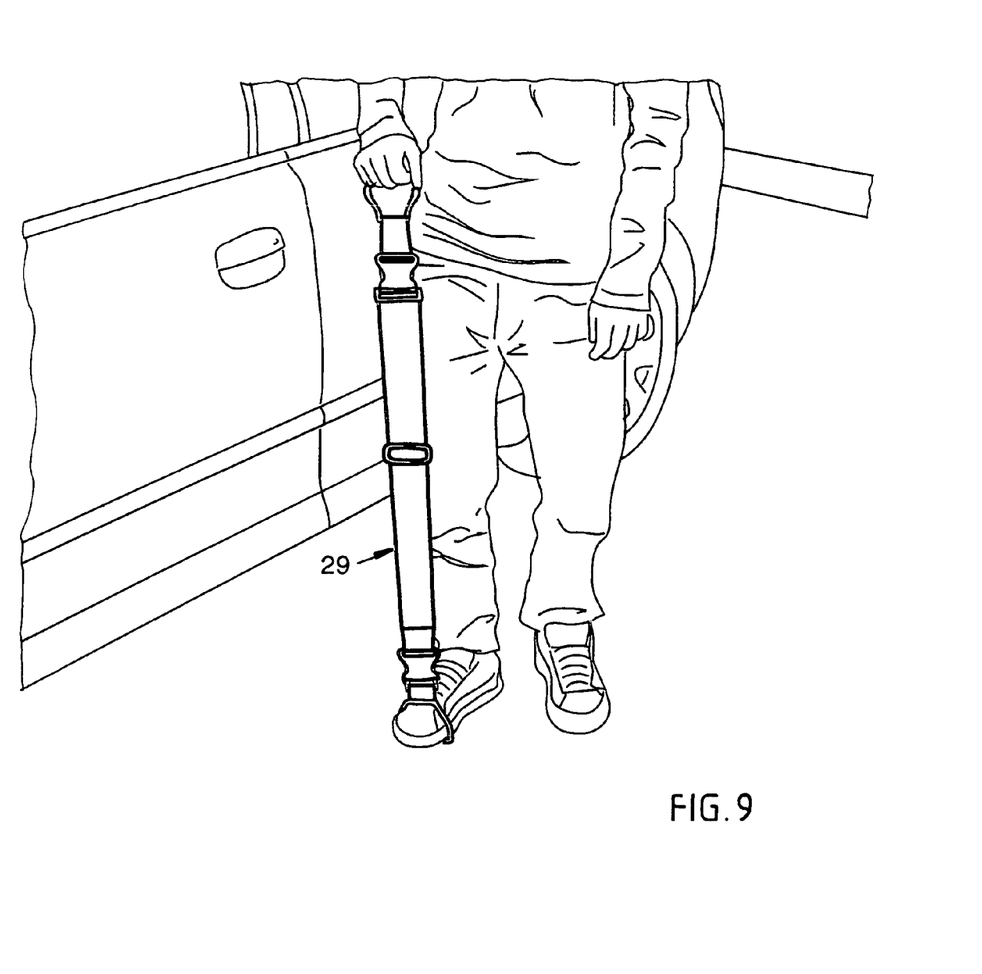

Once tensile belt 2 has been fitted together with the two grip elements 4, 5, an expander 29 is obtained with which various exercises can be performed, for example one-arm or two-arm extensions with the expander 29 in front of the upper body (FIG. 7), two-arm extensions with the expander 29 behind the upper body (FIG. 8), or flexing of the forearm against the tensile force of the expander 29 with its opposite end anchored on one foot (FIG. 9). Whereas the abdominal muscles can be exercised constantly while driving or riding (FIG. 1), the expander exercises are more suitable for breaks in a trip, for example at a rest stop.

The invention claimed is:

1. An apparatus (1) for exercising abdominal muscles in a sitting position, the apparatus comprising: an elastic and expandable tensile belt (2) which is moved by a user by active muscular exertion, and a fastening means (3) for detachably affixing said tensile belt (2) to a backrest (18) of a selected one of a chair, a car seat (19), and other article of seating furniture, wherein said tensile belt (2):
    a) is adapted to elastically constrain the abdominal muscles by exerting tensile force thereon,
    b) is adapted to engagingly encircle the waist of a user over no more than 270°, while a remainder of the waist is embraced by said fastening means (3),
    c) a respective connector element (7, 8) at each end thereof (12, 14), and
    d) an elastic strap (6) extending between said connector elements (7, 8);
    and wherein said fastening means (3)
    e) extend around the backrest (18) of the chair, the car seat (19) or the other article of seating furniture, and
    f) is provided with two mating connector elements (23, 24), each of which is compatible with a respective one of said mating connector elements (7, 8) of said tensile belt (2), and which separate a front part of the fastening means (3) between said connector elements (23, 24) from a back portion of said fastening means (3) beyond said connector elements (23, 24), wherein an elastic region is located at said front part of said fastening means (3), while said back portion of said fastening means (3) is nonelastic and neither stretches nor shifts as the abdominal muscles are exercised.

2. The apparatus in accordance with claim 1, wherein the length of said tensile belt (2) is adjustable.

3. The apparatus in accordance with claim 1, wherein said connector elements (7, 8; 23, 24) for attaching said belt (2) to the backrest (18) are provided with tongue elements (9) that prevent said connector elements (7, 8; 23, 24) from disconnecting on their own.

4. The apparatus in accordance with claim 1, further comprising a lordosis support (20) adapted to be fixed to said tensile belt (2) and to the backrest (18).

5. The apparatus in accordance with claim 4, wherein said lordosis support (20) is disposed between two of said connector elements (23, 24).

6. The apparatus in accordance with claim 4, wherein said lordosis support (20) comprises an inflatable air cushion.

7. The apparatus in accordance with claim 1, wherein said fastening means extends around the backrest (18) and is elastically implemented.

8. The apparatus in accordance with claim 7, wherein said fastening belt for affixing said tensile belt (2) to the backrest (18) is fastened to itself and is adapted to be slipped over the backrest (18).

9. The apparatus in accordance with claim 7, wherein said fastening means for affixing said tensile belt (2) to the backrest (18) is adapted to be fastened to itself and placed around the backrest (18).

10. The apparatus in accordance with claim 1 and further comprising two grip elements (4, 5), each comprising a mating connector element (26, 27), for connection to said mating connector element (7, 8) compatible therewith and disposed at the respective end (12, 14) of said tensile belt (2).

11. The apparatus in accordance with claim 1 wherein said fastening means further comprises a lordosis support.

* * * * *